(12) United States Patent
Noritake

(10) Patent No.: US 6,433,232 B2
(45) Date of Patent: Aug. 13, 2002

(54) PROCESS FOR PRODUCING HYDROXYAROMATIC COMPOUND

(75) Inventor: Tomoyuki Noritake, Ichihara (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/780,484

(22) Filed: Feb. 12, 2001

(30) Foreign Application Priority Data

Feb. 18, 2000 (JP) ........................................ 2000-040767

(51) Int. Cl.$^7$ .............................................. C07C 37/08
(52) U.S. Cl. .................... 568/768; 568/754; 568/798
(58) Field of Search ................ 568/754, 768, 568/798

(56) References Cited

U.S. PATENT DOCUMENTS

| | | | |
|---|---|---|---|
| 2,789,142 A | * | 4/1957 | Graham |
| 3,927,124 A | | 12/1975 | Burkholder |
| 4,119,791 A | * | 10/1978 | Hollingshead |
| 5,510,543 A | * | 4/1996 | Fulmov |

FOREIGN PATENT DOCUMENTS

| | | |
|---|---|---|
| DE | 2 228 286 | 1/1974 |
| EP | 0 028 931 A1 | 5/1981 |

OTHER PUBLICATIONS

Foreign Office Action and Search Report (2001).

* cited by examiner

Primary Examiner—Michael L Shippen
(74) Attorney, Agent, or Firm—Sughrue Mion, PLLC

(57) ABSTRACT

A process for producing a hydroxyaromatic compound by oxidizing an alkyl group-substituted aromatic hydrocarbon to a hydroperoxyaromatic compound and decomposing the hydroperoxyaromatic compound to the hydroxyaromatic compound in which the step of neutralizing the reaction mixture containing the hydroxyaromatic compound with an aqueous alkali solution is conducted so that an aqueous layer, which is obtained by mixing an oil layer of the neutralized mixture and deionized water in a volume ratio of the oil layer to the deionized water of 2:1 to obtain an oil/water mixture and allowing the oil/water mixture to stand still, may have a pH falling within the range of from 4.5 to 5.5, improves the yield of the hydroxyaromatic compound product while suppressing by-production of heavy substances.

1 Claim, No Drawings

PROCESS FOR PRODUCING HYDROXYAROMATIC COMPOUND

FIELD OF THE INVENTION

The present invention relates to a process for producing a hydroxyaromatic compound. In more particular, the invention relates to a process for producing a hydroxyaromatic compound which makes it possible to produce a hydroxyaromatic compound in a high yield.

BACKGROUND OF THE INVENTION

For producing a hydroxyaromatic compound (intended product) such as resorcinol from an alkyl group-substituted aromatic hydrocarbon (starting material) such as 1,3-diisopropylbenzene, there is known, for example, a process comprising the steps of:

(1) oxidizing a starting material liquid containing an alkyl group-substituted aromatic hydrocarbon to obtain a reaction liquid containing a hydroperoxyaromatic compound, (2) decomposing the hydroperoxyaromatic compound in the presence of an acidic substance to obtain a reaction mixture containing a hydroxyaromatic compound, and (3) distilling the reaction mixture to separate the hydroxyaromatic compound from light boiling fractions, thereby to obtain the hydroxyaromatic compound.

However, this process has a disadvantage in that a large amount of heavy substances are by-produced in step (3), resulting in lowering the yield of the intended hydroxyaromatic compound.

SUMMARY OF THE INVENTION

The object of the present invention is to provide a process for producing a hydroxyaromatic compound which can suppress the above-mentioned by-production of heavy substances and resultantly makes it possible to produce the intended hydroxyaromatic compound in a high yield.

The present inventor has made extensive study to find a process for producing hydroxyaromatic compounds which is free from the above-mentioned disadvantage. As a result, he has found that the above-mentioned object of the present invention can be attained by neutralizing the reaction mixture obtained in the above step (2) under specific conditions to obtain a neutralized mixture, separating the neutralized mixture into an oil layer and an aqueous layer, and distilling the oil layer thus separated. The present invention has been accomplished on the basis of the above finding.

Thus, the present invention provides a process for producing a hydroxyaromatic compound comprising the steps of:

(i) oxidizing a starting material liquid containing an alkyl group-substituted aromatic hydrocarbon to obtain a reaction liquid containing a hydroperoxyaromatic compound, (ii) decomposing the hydroperoxyaromatic compound in the presence of an acidic substance to obtain a reaction mixture containing a hydroxyaromatic compound, (iii) neutralizing the reaction mixture with an aqueous alkali solution to obtain a neutralized mixture so that an aqueous layer, which is obtained by mixing an oil layer of the neutralized mixture and deionized water in a volume ratio of the oil layer to the deionized water of 2:1 to obtain an oil/water mixture and allowing the oil/water mixture to stand still, may have a pH falling within the range of from 4.5 to 5.5, (iv) separating the neutralized mixture into an oil layer and an aqueous layer to obtain an oil layer, and (v) distilling the oil layer to separate the hydroxyaromatic compound from light boiling fractions, thereby to obtain the hydroxyaromatic compound.

DETAILED DESCRIPTION OF THE INVENTION

The "alkyl group-substituted aromatic hydrocarbon" referred to in the present invention signifies an aromatic hydrocarbon substituted with at least one $C_{1-10}$ primary, secondary or tertiary alkyl group. The number of the substituent alkyl groups that the aromatic hydrocarbon may have is not particularly limited, but is preferably 1–3. The alkyl group includes, for example, methyl group, ethyl group and isopropyl group. Of these, ethyl group and a secondary or tertiary alkyl group such as the isopropyl group are preferable. The alkyl group-substituted aromatic hydrocarbons include, for example, methylbenzene, ethylbenzene, isopropylbenzene, 1,3-diisopropylbenzene and 1-methyl-3-isopropylbenzene. Of these, ethylbenzene, isopropylbenzene, 1,3-diisopropylbenzene and 1-methyl-3-isopropylbenzene are preferable.

The "hydroperoxyaromatic compound" referred to in the present invention signifies hydroperoxides obtainable by oxidizing alkyl group-substituted aromatic hydrocarbons. When 1,3-diisopropylbenzene is selected as an alkyl group-substituted aromatic hydrocarbon, representative hydroperoxyaromatic compounds obtainable therefrom are as follows.

MHPO: 3-isopropyl-1-(2-hydroperoxy-2-propyl)-benzene,

DHPO: 1,3-di(2-hydroperoxy-2-propyl)benzene,

CHPO: 3-(2-hydroxy-2-propyl)-1-(2-hydroperoxy-2-propyl)benzene.

The methods and conditions used for oxidizing the alkyl group-substituted aromatic hydrocarbon are not particularly limited. A method of oxidation can be, for example, a known one in which oxidation is carried out with oxygen or air. Any known conditions for oxidation can be used. When 1,3-diisopropylbenzene is selected as an alkyl group-substituted aromatic hydrocarbon, for example, it is usually oxidized under the conditions of a temperature of 70–110° C., a pressure of 0–1 MPa (G) and a residence time of 0–50 hours. The reactor includes, for example, a flow-through reaction vessel and reaction tower. The production of a hydroxyaromatic compound is usually conducted by a continuous process, wherein the starting material liquid often contains a recycled liquid containing hydroperoxides and unreacted 1,3-diisopropylbenzene, so that the starting material liquid usually contains the following main components (the weight of the starting material liquid being taken as 100% by weight).

| | |
|---|---|
| 1,3-diisopropylbenzene | 10–40% by weight |
| MHPO | 20–60% by weight |
| DHPO | 0–5% by weight |
| CHPO | 0–10% by weight |

The reaction liquid obtained by the oxidation of the starting material liquid with air usually contains the following main components (the weight of the reaction liquid being taken as 100% by weight).

| 1,3-diisopropylbenzene | 10–40% by weight |
| MHPO | 20–60% by weight |
| DHPO | 3–30% by weight |
| CHPO | 0–10% by weight |

It is possible to obtain the intended hydroperoxy aromatic compound exclusively from this reaction liquid by means of extraction with a solvent etc.

The "hydroxyaromatic compound" referred to in the present invention signifies the intended product obtained by the process comprising the steps (1)–(3) above. When 1,3-diisopropylbenzene is selected as an alkyl group-substituted aromatic hydrocarbon and DHPO is selected as an hydroperoxy aromatic compound, for example, the hydroxyaromatic compound corresponding thereto is resorcinol. In this case, besides resorcinol of the intended product, acetone can be obtained as a by-product.

The "acidic substance" referred to in the present invention signifies a substance which has an effect of decomposing a hydroperoxyaromatic compound into a hydroxyaromatic compound. The kind of the acidic substance is not particularly limited. The acidic substance includes, for example, mineral acids, such as sulfuric acid, sulfuric anhydride, sulfur dioxide, perchloric acid, phosphoric acid, polyphosphoric acid, hydrochloric acid, hydrogen fluoride, phosphotungstic acid and phosphomolybdic acid; sulfonic acids, such as benzenesulfonic acids (e.g., p-toluenesulfonic acid), methanesulfonic acid, trichloromethanesulfonic acid and trifluoromethanesulfonic acid; Lewis acids, such as aluminum chloride, boron trifluoride, boron trifluoride complex, tin chloride, antimony chloride and sulfur tetrafluoride; organic acids, such as trichloroacetic acid, trifluroacetic acid and chloroacetic acid. Preferred acidic substances among these are sulfuric acid, sulfuric anhydride, perchloric acid, boron trifluoride and phosphoric acid.

The conditions in the decomposition by the acidic substance are not particularly limited. For example, when sulfuric anhydride is used as the acidic substance, it is preferable that the molar ratio of the acidic substance used to the hydroperoxide group is not more than 0.003, the temperature is 50–150° C. and the reaction time is not more than 15 minutes.

Step (iii) according to the present invention is a step of neutralizing the reaction mixture obtained by step (ii) with an aqueous alkali solution to obtain a neutralized mixture. The reason for conducting the neutralization is that since the above-mentioned reaction mixture is strongly acidic, when the reaction mixture is distilled (that is, step (v) is conducted) without being subjected to the neutralization, the yield of the hydroxyaromatic compound is lowered and the corrosion of the equipment is promoted.

In the present invention, it is critical to conduct step (iii) under such conditions that an aqueous layer, which is obtained by mixing an oil layer of the neutralized mixture and deionized water in a volume ratio of the oil layer to the deionized water of 2:1 to obtain an oil/water mixture and allowing the oil/water mixture to stand still, may have a pH falling within the range of from 4.5 to 5.5. Other conditions in conducting step (iii) are not particularly limited. When the above-mentioned pH value is less than 4.5, the yield of the hydroxyaromatic compound tends to be low and the corrosion of the equipment tends to be promoted due to insufficient neutralization. When the pH value is higher than 5.5, to the contrary, the amount of the by-produced heavy substances tends to increase and resultantly the yield of the hydroxyaromatic compound of the intended product tends to be low.

The pH value can be maintained within the range of from 4.5 to 5.5 by, for example, the following methods.

(1) a method wherein the oil layer of the neutralized mixture is sampled, the sample is mixed with half a volume of the sample of deionized water, the resulting mixture is allowed to stand still, the pH value of the aqueous layer is measured with a pH water, and the amount of aqueous alkali solution to be added is controlled according to the measured pH value, (2) a method wherein the pH value of the aqueous layer in the neutralized mixture obtained in such an actual process that the pH value of the aqueous layer, obtained when the oil layer in the neutralization mixture is mixed with half a volume of the oil layer of deionized water and the resulting mixture is allowed to stand still, actually falls in the range of 4.5–5.5 is determined beforehand, and the pH value of the aqueous layer in the neutralization mixture obtained in the actual process in question is measured by a pH meter, according to which the amount of aqueous alkali solution to be added is determined.

The kind of the aqueous alkali solution used in the present invention is not particularly limited. The aqueous alkali solution includes, for example, aqueous solutions of NaOH, NaHCO$_3$, Na$_2$CO$_3$, KOH, KHCO$_3$, K$_2$CO$_3$, Ca(OH)$_2$, CaCO$_3$ and NH$_3$. Of these aqueous alkali solution, preferably used in general is an aqueous sodium hydroxide solution. The concentration of alkali in the aqueous alkali solution is not particularly limited.

Step (iv) according to the present invention is the step of separating the neutralized mixture obtained in step (iii) into an oil layer and an aqueous layer to obtain an oil layer. The method for separateing the oil layer from the aqueous layer and the conditions under which the step is conducted are not particularly limited, and known methods and conditions can be adopted.

Step (v) according to the present invention is the step of distilling the oil layer obtained in step (iv) to separate hydroxyaromatic compound and light boiling fractions, such as ketones and solvents, from each other, thereby to obtain the hydroxyaromatic compound. The method of distillation and the conditions under which the step is conducted are not particularly limited, and known methods and conditions can be adopted.

The present invention is described in detail below with reference to Examples, but the invention is not limited thereto.

EXAMPLE 1

1,3-Diisopropylbenzene was oxidized with air to obtain a reaction liquid (step (i)) containing a hydroperoxyaromatic compound. The hydroperoxyaromatic compound in the reaction liquid was extracted with an aqueous alkali solution to obtain extract-1. The hydroperoxyaromatic compound in extract-1 was extracted with methyl isobutyl ketone to obtain extract-2. Extract-2 was distilled to obtain a concentrated liquid containing 20% by weight of 1,3-di(2-hydroperoxy-2-propyl)benzene (DHPO) and 0.3% by weight of 3-(2-hydroxy-2-propyl)-1-(2-hydroperoxy-2-propyl)benzene (CHPO).

Into a reactor equipped with a stirrer and a reflux condenser were fed continuously 800 parts by weight per hour of the above concentrated liquid and 18 parts by weight per hour of a 0.3% by weight acetone solution of sulfuric anhydride, and the mixture was allowed to react at 72° C. and a residence time of 6 minutes, to obtain a reaction mixture (step (ii)).

The reaction mixture was continuously withdrawn from the reactor to a neutralization vessel, while continuously adding a 25% by weight aqueous sodium hydroxide solution by drops into the neutralization vessel, to obtain a neutralization mixture (step (iii)). The amount of the aqueous sodium hydroxide solution added herein was determined such that when the oil layer in the neutralization mixture was mixed with half a volume of the oil layer of deionized water and the resulting mixture was allowed to stand still, the pH value of the aqueous layer obtained might fall within the range of 4.5–5.5.

The neutralized mixture was separated into an oil layer and an aqueous layer, to obtain an oil layer (step (iv)), the oil layer was distilled under conditions of from normal pressure to 60 Torr, to distill out and separate light boiling fractions, acetone and methyl isobutyl ketone, thereby to obtain a bottom containing resorcinol as the main component (step (v)). The content of heavy substances in the bottom was 9.1% by weight.

COMPARATIVE EXAMPLE 1

The same procedures as in Example 1 were repeated except that the aqueous sodium hydroxide solution was added so as to give a pH value not less than 5.5 and not more than 6.5 in step (iii). The content of heavy substances in the bottom was 10.2% by weight.

What is claimed is:

1. A process for producing resorcinol comprising the steps of:
   (i) oxidizing a starting material liquid containing 1,3-diisopropylbenzene to obtain a reaction liquid containing 1,3-diisopropylbenzene peroxide,
   (ii) decomposing the 1,3-diisopropylbenzene peroxide in the presence of sulfuric anhydride to obtain a reaction mixture containing resorcinol,
   (iii) neutralizing the reaction mixture with an aqueous alkali solution to obtain a neutralized mixture so that an aqueous layer, which is obtained by mixing an oil layer of the neutralized mixture and deionized water in a volume ratio of the oil layer to the deionized water of 2:1 to obtain an oil/water mixture and allowing the oil/water mixture to stand still, would have a pH falling within the range of from 4.5 to 5.5,
   (iv) separating the neutralized mixture into an oil layer and an aqueous layer to obtain an oil layer, and
   (v) distilling the oil layer to separate the resorcinol from light boiling fractions, thereby to obtain the resorcinol.

* * * * *